United States Patent [19]

Jen et al.

[11] Patent Number: 5,573,215
[45] Date of Patent: Nov. 12, 1996

[54] CLIP ASSEMBLY FOR CLAMPING A TEST-PIECE WITH TWO END PORTIONS WHICH FORM AN ANGLE THEREBETWEEN

[76] Inventors: Ming-Hwa R. Jen, Dept. of mechanical engineering, National Sun Yac-Sen University, Kaohsiung, Taiwan; Weihwang Lin, Dept. of military engineering, Chinese Military Academy, Feng-Shan, Taiwan, 831

[21] Appl. No.: 382,244

[22] Filed: Feb. 1, 1995

[51] Int. Cl.$^6$ ................................ A47G 1/10
[52] U.S. Cl. ............ 248/316.2; 248/230.2; 248/231.31; 24/115 M; 24/136 R
[58] Field of Search .......... 248/228.2, 229.11, 248/229.21, 230.2, 231.31, 316.2, 316.4; 24/132 WL, 136 B, 136 L, 136 R, 115 M

[56] References Cited

U.S. PATENT DOCUMENTS

| | | | |
|---|---|---|---|
| 1,504,087 | 9/1924 | Brady | 24/136 R |
| 1,930,022 | 10/1933 | Tautz | 24/136 R |
| 1,935,645 | 11/1933 | Lundin | 24/136 R |
| 3,776,586 | 12/1973 | Ahlgren et al. | 24/136 R X |
| 4,823,887 | 4/1989 | Umeda | 248/231.31 X |
| 5,015,023 | 5/1991 | Hall | 24/136 R X |

*Primary Examiner*—Leslie A. Braun
*Assistant Examiner*—Richard M. Smith
*Attorney, Agent, or Firm*—Marshall & Melhorn

[57] ABSTRACT

A clip assembly includes a main block with a tapered internal wall confining a receiving space to receive slidably and engageably a pair of clamps therein. The clamps define a gap therebetween. The clamps further define an elongated engaging groove at its upper portion and extends transversely to the gap which receives engageably two connectors with two connecting rods extending out from the engaging groove to connect a circular disc disposed above the clamps. The disc has a centrally located threaded through-hole. A cover member has a through-hole aligned with the threaded through-hole of the disc and mounted securely on the rigid block to cover the receiving space. A regulating screw has a threaded portion engaged threadedly in the threaded through-hole of the circular disc and a head portion engaged rotatably by the periphery of the through-hole of the cover member so as to prevent the head portion from moving axially when the regulating screw is rotated about its axis.

8 Claims, 6 Drawing Sheets

CLIP ASSEMBLY FOR CLAMPING A TEST-PIECE WITH TWO END PORTIONS WHICH FORM AN ANGLE THEREBETWEEN

BACKGROUND OF THE INVENTION

1. Field of the Invention

The invention relates to a clip assembly, more particularly to a clip assembly which is to be attached to one of a pair of opposedly disposed holders of a tester for clamping a test-piece in order to carry out the testing operation.

2. Description of the Related Art

In order to understand the characteristics of a material, such as tensile strength or wear resistance of said material, a material tester is used in conjunction with a conventional clip assembly to carry out the testing operation. The conventional clip assembly 15 is first attached to one of a pair of opposedly disposed holders of the tester for clamping an end portion of the test-piece 10, as shown in Fig. 1. After the attachment, the orientation of the conventional clip assembly 15 is not adjustable relative to the holder, thus the conventional clip assembly can only clamp the end portion of a straight test-piece. Since the test-piece generally forms an angle between the two end portions thereof, a connector 12 is constructed which has one end clamped by the conventional clip assembly 15 and another end connected to one end portion 14 of the test-piece 10 so as to correct the orientation of said end portion 14 of the test-piece in order to carry out the testing operation.

To construct a connector for every individual testpiece in order to place the end portions of the testpiece at a proper orientation is not convenient for a user, not to mention that in so doing, the results are not precise due to the involvement of the connectors. Moreover, it is time-consuming and increases the expense for carrying out the test.

SUMMARY OF THE INVENTION

Therefore, the main object of this invention is to provide a clip assembly which is to be used in conjunction with a tester for clamping an end portion of a test-piece regardless of whether or not the test-piece has an angle between the two end portions thereof and without the need to employ a connector.

Accordingly, a clip assembly according to the present invention which is to be attached to one of a pair of opposedly disposed holders of a tester for clamping one end portion of a test-piece to carry out a testing operation and includes a main rigid block with an open top. The block has an internal wall and a bottom portion which cooperates with the internal wall to confine a receiving space therein, the internal wall tapering gradually from the open top toward the bottom portion, the bottom portion being provided with an opening communicating the receiving space to an exterior of the rigid block; a pair of symmetric clamps received slidably in the receiving space and defining a gap therebetween for clamping the end portion of the test-piece which is to be inserted into the gap from the exterior via the opening of the bottom, each of the pair of clamps further defining an elongated engaging groove extending transversely to the gap, the grooves being aligned with one another and each of the grooves receiving engageably a connector which has a connecting rod extending out from the engaging groove, a disc being disposed above the pair of clamps and having a threaded through-hole and connected securely with each of the connecting rods of the connectors adjacent to the threaded through-hole; a cover member mounted securely on the rigid block so as to cover the open top of the rigid block, the cover member having a through-hole formed therethrough aligned with the threaded through-hole of the disc; and a regulating screw having a threaded portion engaged threadedly in the threaded through-hole of the circular disc and a head portion engaged rotatably by the periphery of the through-hole of the cover member so as to prevent the head portion from moving axially but permitting the clamp to move axially when the regulating screw is rotated about its axis.

BRIEF DESCRIPTION OF THE DRAWINGS

Other features and advantages of the present invention will become more apparent in the following detailed description of the preferred embodiment with reference to the accompanying drawings, in which.

DETAILED DESCRIPTION OF THE PREFERRED EMBODIMENT

Note that the clip assembly of the present invention is to be attached to one of a pair of opposedly disposed holders of a tester for clamping one end portion of a test-piece. The holders of the tester are movable linearly toward or away relative to one another and permit adjustment of the clip assembly in a certain orientation so as to clamp two end portions of the test-piece for carrying out the testing operations.

Figure 1:
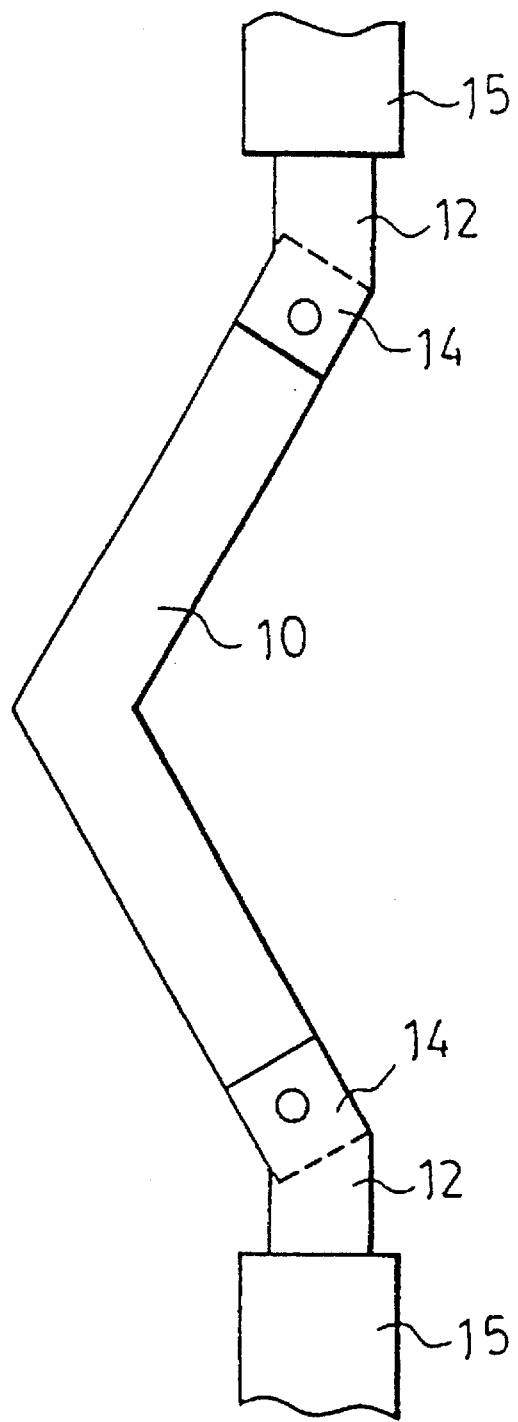
FIG. 1 shows a pair of conventional clip assemblies clamping two end portions of a test-piece in conjunction with a pair of connectors.
Figure 2:
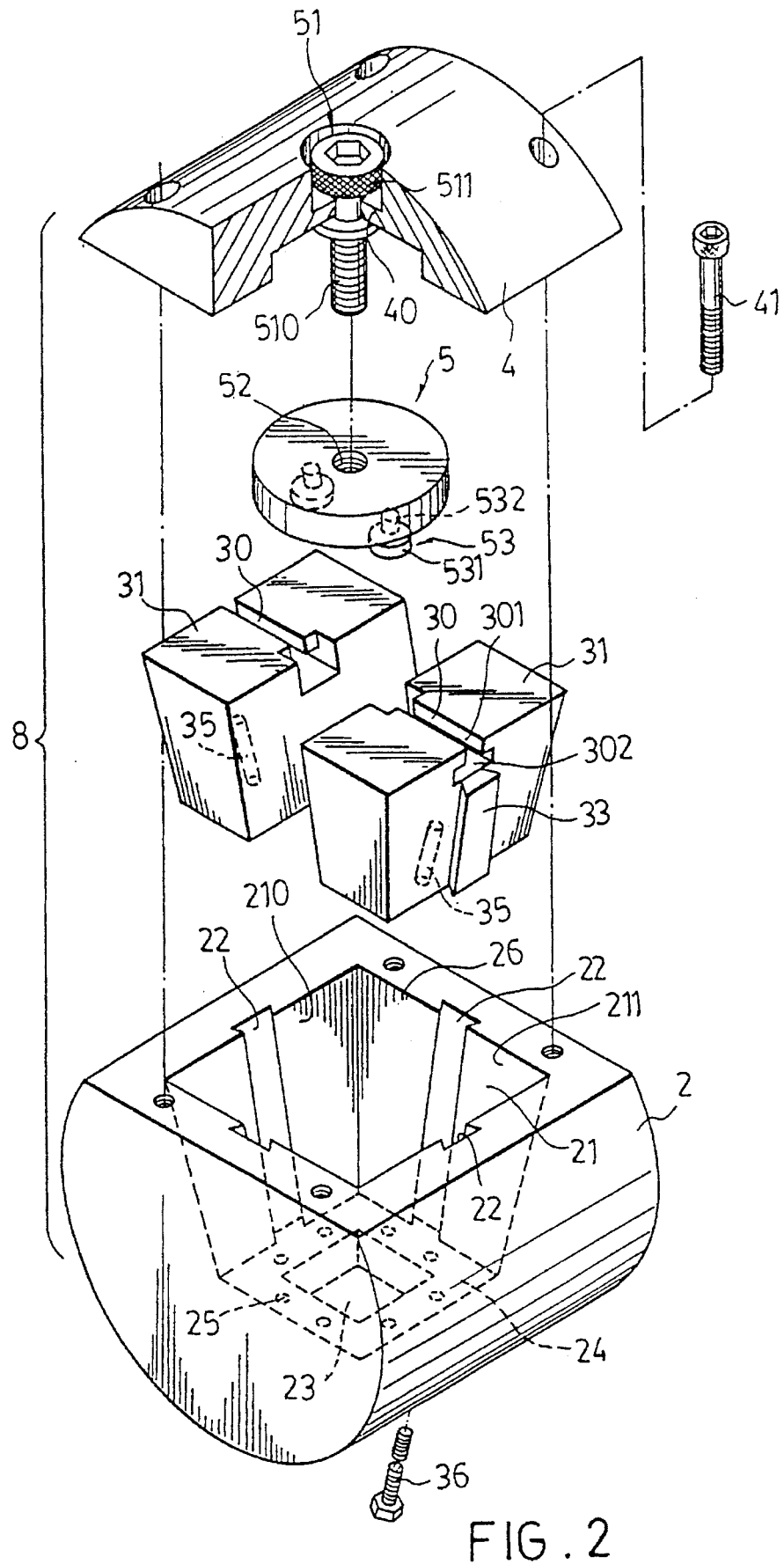
FIG. 2 shows an exploded view of a clip assembly of the present invention for clamping one end portion of a test-piece.
Figure 3:
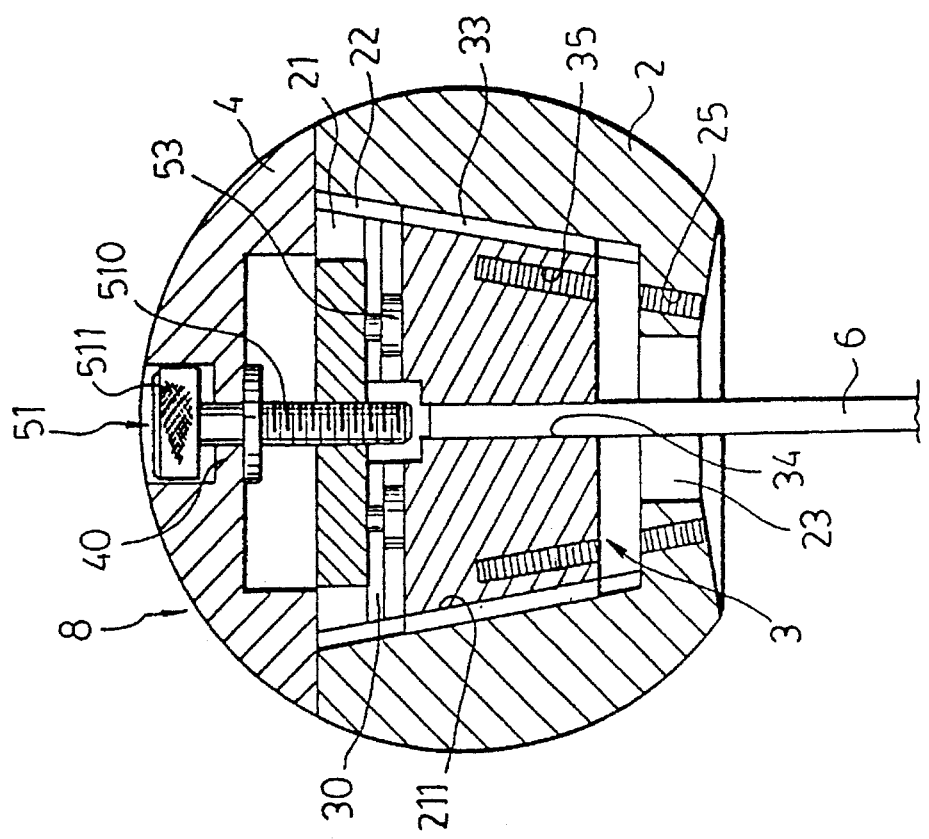
FIG. 3 is a cross-sectional view of the clip assembly of the present invention.

Referring to FIGS. 2 and 3, a preferred embodiment of the clip assembly of the present invention includes a main rigid block 2, a pair of symmetric clamps 3, a cover member 4, a circular disc 5 and a regulating screw 51.

The main block 2 with an open top 26 has an internal wall 21 and a bottom portion 24 which cooperates with the internal wall 21 to define a receiving space 211 therein. The internal wall 21 is constituted by two pairs of opposed walls 210, 211, each of which has a pair of opposed channels 22 formed therein and extends between the open top 26 and the bottom portion 24. The internal wall 21 further tapers gradually from the open top 26 toward the bottom portion 24. The bottom portion 24 is provided with an opening 23 which communicates the receiving space 211 to an exterior of the main rigid block 2. The bottom portion 24 of the rigid block 2 further has a pair of screw holes 25 formed therethrough, the purpose of which will be described in greater detail in the following paragraphs. The symmetric clamps 3 are wedge-shaped and disposed in the receiving space 211 of the main body 2. Each of the wedge-shaped clamps 3 has an elongated projection 33 engaged slidably in a corresponding one of the channels 22 and thus defines in cooperation with the other one of the clamps 3 a gap 34 therebetween. Each of the clamps 3 further has a threaded blind hole 35 formed at a bottom portion thereof which is parallel to a corresponding one of the opposed walls 210, 211 and aligns with a corresponding one of the screw holes 25 formed through the bottom portion 24, as best illustrated in FIG. 3. Each of the clamps 3 further defines an elongated engaging groove 30 which extends transversely to the gap 34, the grooves 30 being aligned with one another. The engaging groove 30 is of an inverted T-shaped cross section with an enlarged lower portion 302 and a constricted upper portion 301 which communicates with the lower portion 302 and opens to an upper side 31 thereof.

The circular disc 5 has a centrally located threaded through-hole 52 and two connectors 53 formed integrally therewith adjacent to the threaded through-hole 52. Each of the connectors 53 has an enlarged head 531 inserted into the enlarged lower 302 portion of the engaging groove 30 while a connecting rod 532 of the connector 53 extends out from the constricted upper portion 301 in such a manner that the circular disc 5 is disposed above the upper side 31 of the clamps 3.

The cover member 4 is mounted securely on the rigid block 2 by screw means 41 such that it covers the open top 26 of the rigid block 2. The cover member 4 has a through-hole 40 formed therethrough and aligned with the threaded through-hole 52 of the circular disc 5.

The regulating screw 51 has a threaded portion 510 engaged threadedly in the threaded through-hole 52 of the circular disc 5 and a H-shaped head portion 511 with a constricted section engaged rotatably by the periphery of the through-hole 40 of the cover member 4. When the regulating screw 51 is rotated about its axis, the circular disc 5 is not rotated synchronously due to the connection thereof with the wedge-shaped clamp 3 via the connectors 53, but rather moves axially and correspondingly permit the wedge-shaped clamps 3 to move together with the disc 5 slidingly along the channel 22 of the internal wall 21, thereby changing the size of the gap in order to clamp an end portion of test-pieces of different thicknesses.

Figure 4:
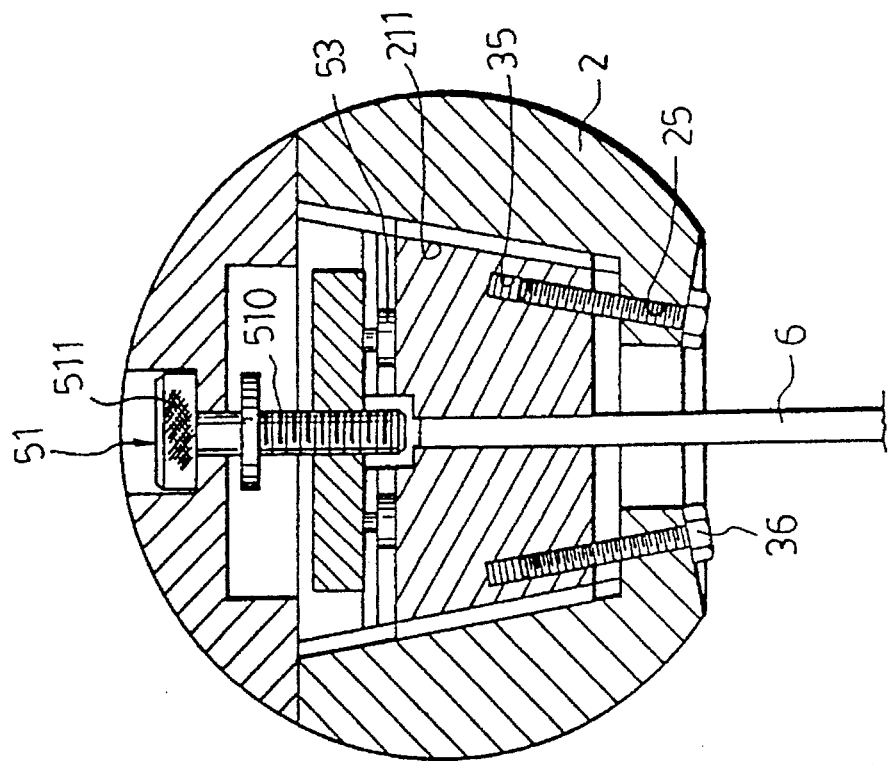
FIG. 4 shows a cross-sectional view of the clip assembly of the present invention, illustrating the manner in which the clamps employed in the assembly is secured to the main body by the use of a pair of screws.

Referring again to FIG. 3, the gap 34 defined by the wedge-shaped clamps 3 can be adjusted by rotation of the regulating screw 51 in order to clamp the end portion of the test-piece 6 of a different thickness, and a pair of locking screws 36 can be inserted via the screw holes 25 of the bottom portion 24 of the main block 2 so as to engage threadedly in the threaded blind holes 35 of the clamps 3, as shown in FIG. 4. Thus, two end portions of the test-piece 6 are clamped securely by a pair of clip assemblies of the present invention to be subjected to the testing operation, such as tension, compression, and fatigue.

Figure 5:
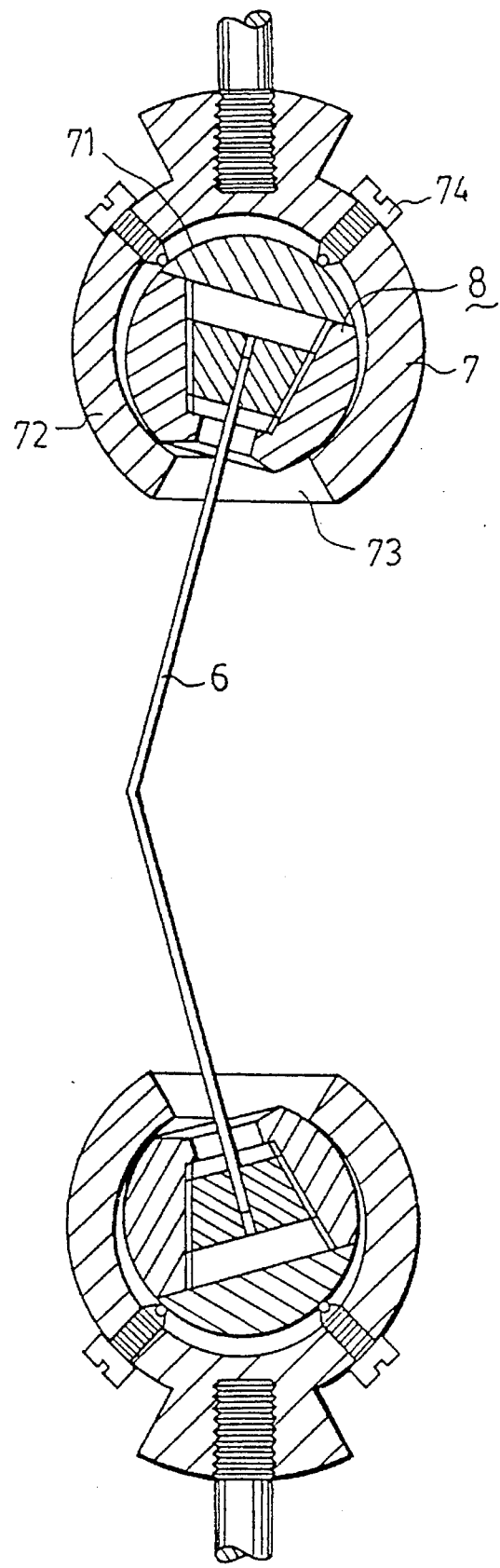
FIG. 5 shows a pair of clip assemblies of the present invention attached to a pair of opposedly disposed holders of a tester and clamping a test-piece therebetween.

Referring to FIGS. 2 and 5, note that the preferred embodiment of this invention is cylindershaped or sphere-shaped such that the clip assembly 8 can be disposed in a holder 7 of a tester (not shown). The holder 7 confines a cylinder-shaped receiving space 71 therein which is adapted to receive rotatably the clip assembly 8 therein. The holder 7 has a bottom portion 72 with an opening 73 formed therethrough for extension of the end portion of the test-piece 6. After adjusting the orientation of the end portions of the test-piece 6 relative to the holders 7, the clip assemblies 8 are secured in the holders 7 by the tightening action of the locking screws 74 which pass through the holders 7.

Figure 6:
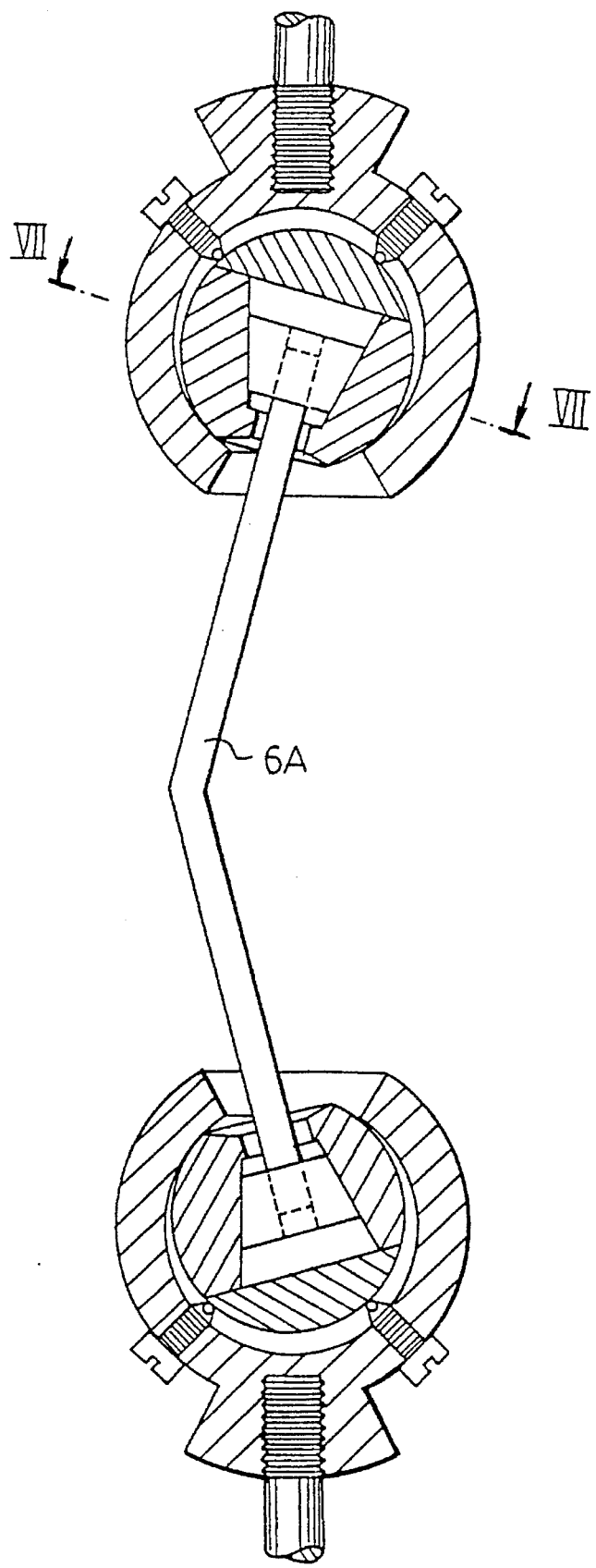
FIG. 6 shows a pair of clip assemblies of the present invention attached to a pair of opposedly disposed holders of a tester and clamping a test-piece of a form different from the one shown in FIG. 5.

FIG. 6 shows a pair of clip assemblies of the present invention clamping two end portions of a testpiece 6A which has an angle formed between the end portions different from that of the test-piece 6 of FIG. 5 and a thickness that is thicker than the testpiece 6 shown in FIG. 6.

Figure 7:
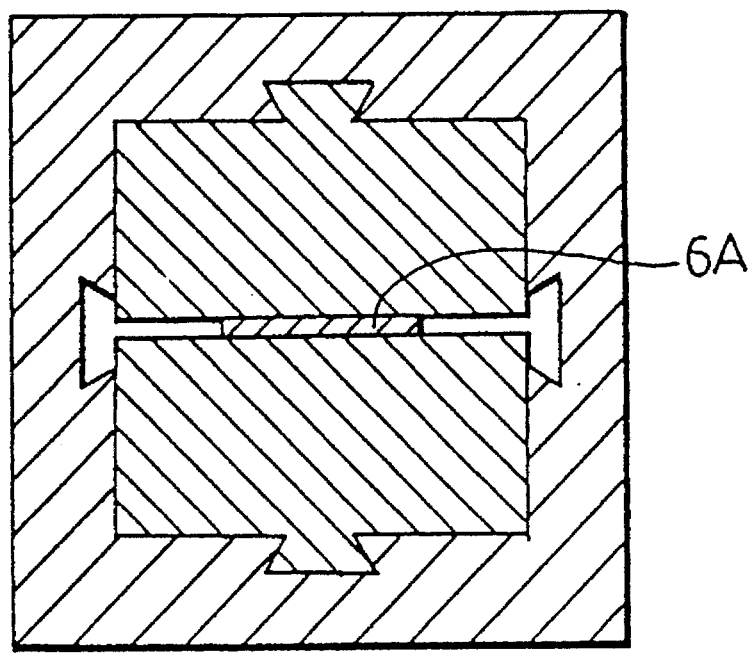
FIG. 7 is a cross-sectional view of FIG. 6 taken along the lines VII-VII.

Referring to FIG. 7, in the event that the end portions of the test-piece 6A require the pair of clamps 3 to be rotated 90' which only then can the clip assemblies of the present invention clamp the end portions, the pair of clamps 3 in FIG. 2 can be rotated 90' and thus engage with the remaining pair of channels 22. The dotted lines show the positions of the pair of clamps before rotation.

The external surface constituted cooperatively by the rigid block 2 and the cover member 4 of the clip assembly of the present invention can also be constructed in the shape of a ball and the holder of the tester can be formed with a ball-shaped receiving space such that the clip assembly can be rotated more freely in the holder, thereby the test-piece can be disposed at any desired orientation.

From the above explanation, it can be appreciated that the clip assembly according to the present invention can clamp securely one end portion of a testpiece regardless of the angle formed between the two end portions thereof and without the need to employ a connector as in the conventional clip assembly. Thus the testing operation is facilitated with the use of the clip assembly of the present invention.

With the present invention thus explained, it is obvious to those skilled in the art that various modifications and variations can be made without departing from the scope and spirit thereof. It is therefore intended that this invention be limited only as in the appended claims.

We claim:

1. A clip assembly comprising:

a main rigid block with an open top having an internal wall and a bottom portion which cooperates with said internal wall to confine a receiving space therein, said internal wall tapering gradually from said open top toward said bottom portion, said bottom portion being provided with an opening providing communication between said receiving space and an exterior of said rigid block;

a pair of symmetric clamps received slidably in said receiving space and defining a gap therebetween for clamping one end portion of a test-piece which is to be inserted into said gap from said exterior via said opening of said bottom portion, each of said pair of clamps further defining an elongated engaging groove extending transversely to said gap, said elongated grooves being aligned with one another and receiving respectively and engageably a connector which has a connecting rod extending out from said engaging groove, a disc being disposed above said pair of clamps and having a threaded through-hole and connected securely with each of said connecting rods of said connectors adjacent to said threaded through-hole;

a cover member mounted securely on said rigid block so as to cover said open top of said rigid block, said cover member having a through-hole formed therethrough aligned with said threaded through-hole of said disc; and a regulating screw having a threaded portion engaged threadedly in said threaded through-hole of said disc and a head portion engaged rotatably by a periphery which confines said through-hole of said cover member so as to prevent said head portion from moving axially when said regulating screw is rotated about its axis.

2. The clip assembly as defined in claim 5, wherein said internal wall comprises two pairs of opposed walls, one pair of which has a pair of opposed channels formed therein and extending between said open top and said bottom portion, and said pair of clamps being wedge-shaped and having respectively an elongated projection engaging in and slidable along a corresponding one of said channels.

3. The clip assembly as defined in claim 5, wherein said engaging groove of each of said clamps has an inverted T-shaped cross section with an enlarged lower portion and a constricted upper portion communicating with said lower portion and which is open at an upper side thereof, each of said connectors including an enlarged head connected integrally with said connecting rod and being received engageably in said enlarged lower portion of said engaging groove with said connecting rod extending through said constricted upper portion.

4. The clip assembly as defined in claim 7, wherein each of said clamps further has a threaded blind hole formed at a bottom portion thereof and parallel to a corresponding one of said opposed walls, said bottom portion of said rigid block further having a pair of screw holes formed therethrough respectively aligned with said threaded blind holes, whereby a pair of locking screws can be inserted via said screw holes so as to be engaged threadedly in said threaded blind holes of said clamps.

5. A clip assembly to be attached to one of a pair of oppositely disposed holders of a tester for clamping a test-piece which has first and second end portions and which forms an angle between said first and second end portions, said holder permitting adjustment of said clip assembly in a certain orientation so as to clamp one of said first and second end portions of said test-piece and said holder being movable linearly toward or away relative to the other holder for holding another one of said clip assembly in order to clamp the other one of said first and second end portions, said clip assembly comprising:

a main rigid block with an open top having an internal wall and a bottom portion which cooperates with said internal wall to confine a receiving space therein, said internal wall tapering gradually from said open top toward said bottom portion, said bottom portion being provided with an opening providing communication between said receiving space and an exterior of said rigid block;

a pair of symmetric clamps received slidably in said receiving space and defining a gap therebetween for clamping one of said first and second end portions of said test-piece which is to be inserted into said gap from said exterior via said opening of said bottom, each of said pair of clamps further defining an elongated engaging groove extending transversely to said gap, said engaging grooves being aligned with one another and receiving respectively and engageably a connector which has a connecting rod extending out from said engaging groove, a disc being disposed above said pair of clamps and having a threaded through-hole and connected securely with each of said connecting rods of said connectors adjacent to said threaded through-hole;

a cover member mounted securely on said rigid block so as to cover said open top of rigid block, said cover member having a through-hole formed therethrough and aligned with said threaded through-hole of said disc; and a regulating screw having a threaded portion engaged threadedly in said threaded through-hole of said disc and a head portion engaged rotatably by a periphery which confines said through-hole of said cover member so as to prevent said head portion from moving axially when said regulating screw is rotated about its axis.

6. The clip assembly as defined in claim 1, wherein said internal wall comprises two pairs of opposed walls, one pair of which has a pair of opposed channels formed therein and extending between said open top and said bottom portion, and said pair of clamps being wedge-shaped and having respectively an elongated projection engaging in and slidable along a corresponding one of said channels.

7. The clip assembly as defined in claim 1, wherein said engaging groove of each of said clamps has an inverted T-shaped cross section with an enlarged lower portion and a constricted upper portion communicating with said lower portion and which is open to an upper side thereof, each of said connectors including an enlarged head connected integrally with said connecting rod and being received engageably in said enlarged lower portion of said engaging groove with said connecting rod extending through said constricted upper portion.

8. The clip assembly as defined in claim 7, wherein each of said clamps further has a threaded blind hole formed at a bottom portion thereof and parallel to a corresponding one of said opposed walls, said bottom portion of said rigid block further having a pair of screw holes formed therethrough which are respectively aligned with said threaded blind holes, whereby a pair of locking screws can be inserted via said screw holes to be engaged threadedly in said threaded blind holes of said clamps.

* * * * *